United States Patent [19]

Kleinschroth et al.

[11] Patent Number: 4,912,107

[45] Date of Patent: Mar. 27, 1990

[54] PYRROLOCARBAZOLE DERIVATIVES, COMPOSITIONS CONTAINING THEM, AND METHODS FOR USING THEM

[75] Inventors: Jürgen Kleinschroth, Denzlingen; Johannes Hartenstein, Stegen-Wittental; Christoph Schächtele, Freiburg; Claus Rudolph, Vörstetten; David J. Dooley, Freiburg; Günther Weinheimer, Denzlingen, all of Fed. Rep. of Germany

[73] Assignee: Goedecke Aktiengesellschaft, West Berlin, Fed. Rep. of Germany

[21] Appl. No.: 412,705

[22] Filed: Sep. 26, 1989

[30] Foreign Application Priority Data

Sep. 29, 1988 [DE] Fed. Rep. of Germany ....... 3833008

[51] Int. Cl.$^4$ ................... A61K 31/40; A61K 31/535; C07D 209/56; C07D 413/06
[52] U.S. Cl. ............................. 514/232.5; 514/228.2; 514/232.8; 514/253; 514/316; 514/322; 514/410; 544/58.5; 544/80; 544/121; 544/131; 544/142; 544/357; 544/364; 544/372; 546/187; 546/199; 548/421; 548/423
[58] Field of Search ................ 544/58.5, 80, 121, 131, 544/142, 357, 364, 372; 546/187, 199; 548/421, 423; 514/228.2, 232.5, 232.8, 253, 316, 322, 410

[56] References Cited

PUBLICATIONS

Reed et al, Chemical Abstracts, vol. 96 (1982), No. 199,467t.

Primary Examiner—Robert W. Ramsuer
Attorney, Agent, or Firm—Elizabeth M. Anderson

[57] ABSTRACT

The invention concerns new pyrrolocarbazole derivatives of formula

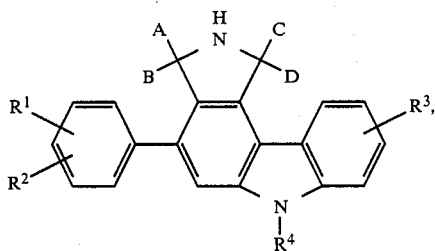

processes for their preparation, as well as medicaments containing these for the inhibition of protein kinases, such as protein kinase C, and thus for the prevention and/or treatment of heart and blood vessel diseases, such as thromboses, arterioscleroses, hypertension, of inflammatory processes, allergies, cancers, and certain degenerative damages of the central nervous system as well as for the treatment of viral diseases.

6 Claims, No Drawings

PYRROLOCARBAZOLE DERIVATIVES, COMPOSITIONS CONTAINING THEM, AND METHODS FOR USING THEM

BACKGROUND OF THE INVENTION

Protein kinase C plays an important role in the intracellular signal transduction and is closely linked with the regulation of contractile, secretory, and proliferative processes.

SUMMARY OF THE INVENTION

The present invention covers new pyrrolocarbazole derivatives of formula

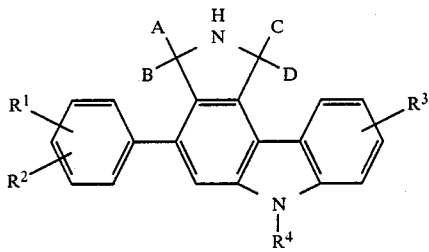

or a pharmaceutically acceptable salt thereof wherein A, B, C, D, $R^1$, $R^2$, $R^3$, and $R^4$ are as described below.

DETAILED DESCRIPTION

The present invention concerns new pyrrolocarbazole derivatives of

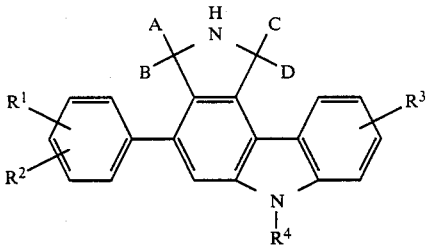

or a pharmaceutically acceptable salt thereof wherein A and B or C and D are either the same and are hydrogen or together form a carbonyl oxygen atom or are different, and one of the residues of A and B or of C and D is hydrogen and the other of the two residues is hydroxyl, with the proviso that at least one of A and B or C and D together form a carbonyl oxygen atom.

$R^1$, $R^2$, and $R^3$ are each independently hydrogen, halogen, especially fluorine, chlorine or bromine, alkyl of from 1 to 4 carbon atoms, nitro, trifluoromethyl, amino, unsubstituted or substituted by: alkyl of from 1 to 4 carbon atoms or benzyl, alkoxy of from one to four carbon atoms, hydroxyl, acyl of from one to four carbon atoms or aminoalkoxy of from one to 12 carbon atoms, unsubstituted or substituted on the alkyl chain by: alkyl of from one to four carbon atoms, hydroxyl or alkoxy of from one to four carbon atoms, and/or substituted on the nitrogen by alkyl of from one to four carbon atoms or benzy or in the case of the two substituents on the nitrogen atom or one substituent on the nitrogen atom with a substituent of the alkyl chain and together with the nitrogen atom form a heterocyclic ring with three to six carbon atoms which can also contain oxygen, a sulphur, and/or further nitrogen atoms and can be substituted by alkyl of from one to four carbon atoms.

$R^4$ is hydrogen, straight-chained or branched alkyl of from one to six carbon atoms, cyanoalkyl of from two to four carbon atoms, alkoxycarbonyl alkyl of from three to seven carbon atoms or aminoalkyl of from one to 12 carbon atoms, unsubstituted or substituted on the alkyl chain by: alkyl of from one to four carbon atoms, hydroxyl or alkoxy of from one to four carbon atoms, and/or substituted on the nitrogen atom by alkyl of from one to four carbon atoms or benzyl. In the case of the two substituents on the nitrogen atom or one substituent on the nitrogen atom with a substituent of the alkyl chain and together with the nitrogen atom form a heterocyclic ring with three to six carbon atoms, which can also contain oxygen, sulphur, and/or further nitrogen atoms and can be substituted by alkyl of from one to four carbon atoms.

Processes for the preparation of a compound of formula I or of regioisomeric mixtures of two of these compounds are also included in the invention. Compositions containing at least one of the compound of formula I are also included in the invention. Methods of using the compound are also included.

Preferred compounds of formula I are those in which $R^1$, $R^2$, and $R^3$ are either the same or different and are hydrogen, fluorine, chlorine, bromine, trifluoromethyl, hydroxyl, nitro, methyl, ethyl, n-propyl, isopropyl, n-butyl, amino, methoxy, ethoxy, aminoethoxy, aminopropoxy, dimethylaminoethoxy, dimethylaminopropoxy, diethylaminoethoxy, N-benzy-N-methylaminoethoxy, N-benzyl-N-methylaminopropoxy, dimethylaminohydroxypropoxy, piperidinoethoxy, piperidinopropoxy, pyrrolidinoethoxy, pyrrolidinopropoxy, morpholinoethoxy, morpholinopropoxy, pyrrolidinylmethoxy, piperidinylmethoxy, N-methylpiperidinylmethoxy, N-methylpyrrolidinylmethoxy, dimethylaminomethoxypropoxy, formyl, acetyl, propionyl or a butyryl group and $R^4$ is hydrogen, methyl, ethyl, n-propyl, isopropyl, n-butyl, cyanomethyl, cyanomethyl, methoxycarbonylethyl, ethoxycarbonylethyl, methoxycarbonylmethyl aminoethyl, aminopropyl, dimethylaminoethyl, dimethylaminopropyl, diethylaminoethyl, N-benzyl-N-methylaminoethyl, N-benzyl-N-methylaminopropyl, dimethylaminohydroxypropyl, diethylaminohydroxypropyl, piperidinoethyl, piperidinopropyl, pyrrolidinoethyl, pyrrolidinopropyl, morpholinoethyl, morpholinopropyl, pyrrolidinylmethyl, piperidinylmethyl, N-methylpiperidinylmethyl, dimethylaminomethoxypropyl, diethylaminomethoxypropyl or N-methyl-pyrrolidinylmethyl.

More preferred compounds of the instant invention are those of formula I wherein $R^1$ and $R^2$ are each independently hydrogen, 2-methyl, 2-chloro, 3-chloro, 4-chloro, 2-bromo, 2-methoxy, 3-methoxy, 4-methoxy, 2-fluoro, 2-trifluoromethyl, 2-amino, 2-nitro, 2-hydroxy, 2-(3-dimethylaminopropoxy) or $R^1$ is 2-nitro and $R^2$ is 5-methoxy and $R^4$ is 2-aminoethyl, 3-aminopropyl, 1-amino-2-propyl, -2-dimethylaminoethyl, 3-dimethylamino-1-propyl, 3-dimethylamino2-propyl, 2-diethylaminoethyl, 2-[N-benzyl-N-methylamino]-ethyl, 3-N-benzyl-N-methylamino]-propyl, 3-dimethylamino-2-hydroxy-1-propyl, 3-diethylamino-2-hydroxy-l-propyl, 2-piperidinoethyl, 3-piperidinopropyl, 2-pyrrolidinoethy, 3-pyrrolidinopropyl, 2-morpholinoethyl, 3-morpholinopropyl, piperidin-2- ylmethyl, N-methylpiperidin-2-ylmethyl, 2-methoxy-1-propyl, pyrrolidin-2-ylmethyl or an N-methylpyrrolidin-2-ylmethyl group, methyl, ethyl, n-propyl, isopropyl, n-butyl, cyanomethyl, 2-cyanoethyl, 2-methoxycarbonylethyl, 2-ethoxycarbonylethyl, and methoxycarbonylmethyl.

The most preferred compounds of the instant invention are those selected from:

1,2,3,6-tetrahydro-1,3-dioxo-4-phenylpyrrolo[-3,4-c]carbazole,
1,2,3,6-tetrahydro-4-(2-methoxyphenyl)1,3-dioxopyrrolo[3,4-c]carbazole,
6-ethyl-1,2,3,6-tetrahydro-1,3-dioxo-4-phenylpyrrolo[3,4-c]carbazole,
4-(2-chlorophenyl)-6-ethyl-1,2,3,6-tetrahydro-1,3-dioxopyrrolo[3,4-c]carbazole,
4-(4-chlorophenyl)-6-ethyl-1,2,3,6-tetrahydro-1,3-dioxopyrrolo[3,4-c]carbazole,
4-(3-chlorophenyl)-6-ethyl-1,2,3,6-tetrahydro-1,3-dioxopyrrolo[3,4-c]carbazole,
4-(2-chlorophenyl)-1,2,3,6-tetrahydro-6-methyl-1,3-dioxopyrrolo[3,4-c]carbazole,
1,2,3,6-tetrahydro-6-methyl-4-phenyl-1,3-dioxopyrrolo[3,4-c]carbazole,
4-(2-chlorophenyl)-1,2,3,6-tetrahydro-1,3-dioxopyrrolo[3,4-c]carbazole,
1,2,3,6-tetrahydro-4-(2-nitrophenyl)-1,3-dioxopyrrolo3,4-c]carbazole,
4-(4-chlorophenyl)-1,2,3,6-tetrahydro-6-methyl-1,3-dioxopyrrolo[3,4-c]carbazole,
4-(3-chlorophenyl)-1,2,3,6-tetrahydro-6-methyl-1,3-dioxopyrrolo[3,4-c]carbazole,
4-(2-trifluoromethylphenyl)-1,2,3,6-tetrahydro-6-methyl-1,3-dioxo-pyrrolo[3,4-c]carbazole,
1,2,3,6-tetrahydro-4-(2-methoxyphenyl)-3-oxopyrrolo-[3,4-c]carbazole,
1,2,3,6-tetrahydro-3-oxo-4-phenylpyrrolo[3,4-c]carbazole,
4-(2-chlorophenyl)-6-ethyl-1,2,3,6-tetrahydro-3-oxopyrrolo[3,4-c]carbazole,
4-(2-chlorophenyl)-6-ethyl-1,2,3,6-tetrahydro-1-hydroxy-3-oxopyrrolo[3,4-c]carbazole,
4-(2-chlorophenyl)-6-ethyl-1,2,3,6-tetrahydro-3-hydroxy-1-oxopyrrolo[3,4-c]carbazole,
1,2,3,6-tetrahydro-4-(2-hydroxyphenyl)-3-oxopyrrolo[3,4-c]carbazole,
4-[2-(3-dimethylaminopropoxy)-phenyl]-6-(3-dimethylaminopropyl)-1,2,3,6-tetrahydro-3-oxopyrrolo[3,4-c]carbazole dihydrochloride,
4-(2-aminophenyl)-1,2,3,6-tetrahydro-1,3-dioxopyrrolo[3,4-c]carbazole,
4-(4-chlorophenyl)-6-ethyl-1,2,3,6-tetrahydro-1-hydroxy-3-oxopyrrolo[3,4-c]carbazole,
4-(4-chlorophenyl)-6-ethyl-1,2,3,6-tetrahydro-3-hydroxy-1-oxopyrrolo[3,4-c]carbazole,
6-(3-dimethylaminopropyl)-1,2,3,6-tetrahydro-1,3-dioxo-4-phenyl-pyrrolo[3,4-c]carbazole,
4-(2-chlorophenyl)-1,2,3,6-tetrahydro-6-(2-morpholinoethyl)-1,3-dioxo-pyrrolo[3,4-c]carbazole,
4-(2-chlorophenyl)-6-(2-diethylaminoethyl)-1,2,3,6-tetrahydro-1,3-dioxo-pyrrolo3,4-c]carbazole,
4-(2-chlorophenyl)-6-(3-dimethylaminopropyl)-1,2,3,6-tetrahydro-1,3-dioxo-pyrrolo[3,4-c]carbazole,
6-(3-dimethylaminopropyl)-1,2,3,6-tetrahydro-1,3-dioxo-4-(2-trifluoromethylphenyl)-pyrrolo3,4-c]carbazole,
4-(2-chlorophenyl)-6-(3-dimethylamino-2-methoxy-1-propyl)-1,2,3,6-tetrahydro-1,3-dioxo-pyrrolo[3,4-c]carbazole,
4-(2-chorophenyl)-1,2,3,6-tetrahydro-1,3-dioxo-6-(2-pyrrolidinoethyl)-pyrrolo[3,4-c]carbazole,
6-(3-dimethylaminopropyl)-1,2,3,6-tetrahydro-4-(2-methylphenyl)-1,3-dioxo-pyrrolo[3,4-c]carbazole,
6-(3-dimethylaminopropyl)-4-(2-fluorophenyl)-1,2,3,6-tetrahydro-1,3-dioxo-pyrrolo[3,4-c]carbazole,
6-(3-diethylamino-2-hydroxy-1-propyl)-1,2,3,6-tetrahydro-1,3-dioxo-4-phenyl-pyrrolo[3,4-c]carbazole,
6-(2-cyanoethyl)-1,2,3,6-tetrahydro-4-(2-methylphenyl)-1,3-dioxo-pyrrolo3,4-c]carbazole,
6-(2-cyanoethyl)-1,2,3,6-tetrahydro-1,3-dioxo-4-phenyl-pyrrolo[3,4-c]carbazole, and
6-(2-cyanoethy)-4-(2-fluoropheny)-1,2,3,6-tetrahydro-1,3-dioxo-pyrrolo[3,4-c]carbazole.

A pharmaceutical composition for preventing and/or treating heart and blood vessel diseases such as thrombosis, arteriosclerosis, and hypertension is also included in the invention.

Pharmaceutical compositions for treating inflammatory processes, for treating allergies, for treating cancers, for treating certain degenerative processes of the central nervous system, and for treating viral diseases are also included in the invention.

A method for preventing and/or treating disease of the heart and blood vessels which comprises treating a mammal suffering therefrom with the above pharmaceutical composition in unit dosage form is also included in the invention.

Methods for treating inflammatory processes, allergies, cancers, certain degenerative processes of the central nervous system, and viral diseases are also included in the invention.

The following processes described the preparation of compounds of formula I.

A) Compounds of formula I in which not only A and B but also C and D form a carbonyl oxygen atom and $R^4$ is hydrogen (compounds Ia) can be prepared according to Scheme I in that one reacts the 1-aryl-4-(2-nitroaryl)-1,4-butadienes (*Tetrahydron Lett* 1983, 1441) of formula II, in which $R^1$, $R^2$, and $R^3$ have the above meaning, obtainable according to known processes, by cycloaddition with maleinimide to compounds of the general formula III. For the case that either $R^1$ or $R^2$ is a 2-nitro group, this reaction is known (*Tetrahydron Lett*, 1983, 1441). Compounds of formula III are dehydrogenated according to conventional processes, e.g., with 2,3-dichloro-5,6-dicyano-p-benzoquinone (DDQ), sulfur, or palladium on active charcoal, to compounds IV. By heating compounds IV with phosphorus (III) compounds, such as triphenyl phosphine or triethyl phosphite, in a suitable inert solvent (*Quart Reviews*, 1968, 22, 222; *Synthesis*, 1969, 11), new pyrrolocarbazole derivatives Ia are produced; see Scheme I below.

Scheme I

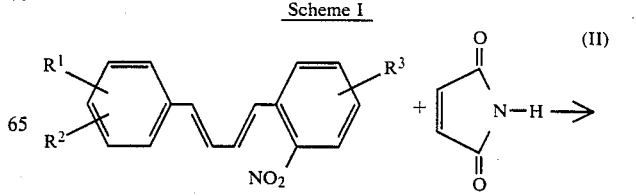

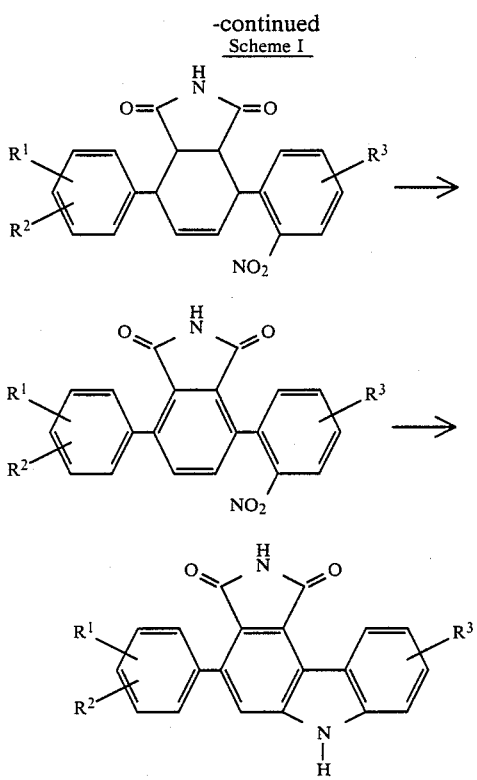

-continued
Scheme I (III)

(IV)

(Ia)

(B) Compounds of formula I, in which not only A and B but also C and D form a carbonyl oxygen atom and $R^1$, $R^2$, $R^3$, and $R^4$ possess the above meanings (compounds Ib), can be prepared according to Scheme II below, in that one reacts unsubstituted or substituted indole-2-aldehydes or derivatives of formula V substituted on the indole nitrogen atom, in which $R^3$ and $R^4$ possess the above meaning, by a Witting reaction with suitably substituted arylmethyl-triphenylphosphonium halides of formula VI, in which $R^1$ and $R^2$ have the above meaning and X signifies halogen, preferably chlorine or bromine, in the presence of suitable bases, such as e.g., alkali metal carbonates, alcoholates, amides or organolithium compounds, to 2-(2-arylvinyl)-indoles of formula VII. Other suitable processes for the preparation of compounds of formula VII have been described (*Chem Comm*, 1970, 1095; *Can J Chem*, 1973, 792; *Tetrahydron Lett*, 1984, 3101). Depending upon the reaction conditions, the compounds of formula VII are obtained as cis/trans isomer mixtures which can be separated by usual processes, such as crystallization or chromatography.

Compounds of formula VII, in which $R^4$ is an aminoalkyl group with one to 12 carbon atoms as defined above or is a cyanoalkyl group with two to four carbon atoms are prepared, preferably by aminoalkylation or cyanoalkylation of compounds of formula VII, in which $R^4$ is hydrogen, by methods of aminoalkylation or cyanoalkylation of indole derivatives known per se. Compounds of formula VII, in which $R^4$ is hydrogen, on acrylnitril in the presence of a basic catalyst (e.g., 1,8-diazobicyclo[5,4,o]undec-7-en =DBU) in a manner known per se (see *J Med Chem*, 1989, 32, 73).

Compounds of formula VII, in which $R^4$ is a 2-alkoxycarbonylethyl group with up to seven carbon atoms, are prepared preferably by Michael addition of compounds of formula VII in which $R^4$ is hydrogen, on acrylic acid ester with up to seven carbon atoms in the presence of a basic catalyst (e.g., 1,8-diazobicyclo[5,-4,o]undec-7-en =DBU) in a manner known per se.

The trans isomers of compounds of formula VII are converted by heating with maleinimide in a suitable solvent into the compounds of formula VIII. The cis isomers of compounds of formula VII or isomerie mixtures thereof are converted into the compounds of formula VIII with maleinimide in a suitable solvent, with the addition of catalysts, such as aluminum trichloride. Cycloadditions of 2-vinylindolenes with suitable dienophils, inter alia also with substituted maleinimides, have been described (*Heterocycles*, 1988, 1253; *Heterocycles*, 1988, 967; *Can J Chem*, 1982, 419). Compounds of formula VIII are dehydrogenated according to conventional processes, e.g., with 2,3-dichloro5,6-dicyano-p-benzoquinone, palladium on active charcoal, sulfur or sodium nitrite in glacial acetic acid to the new pyrrolocarbazole derivatives of formula Ib; see Scheme II below.

Scheme II

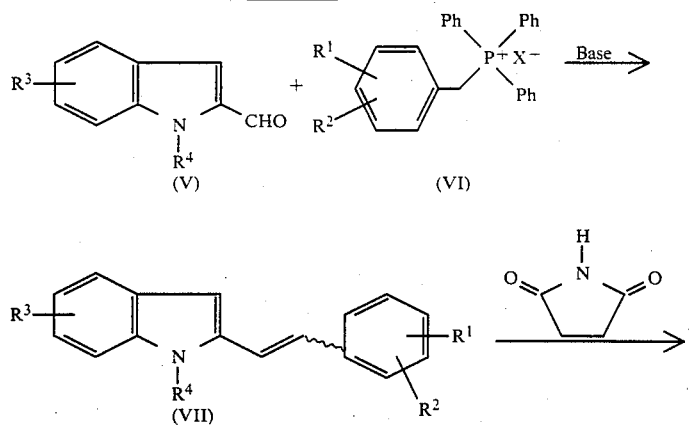

-continued

Scheme II

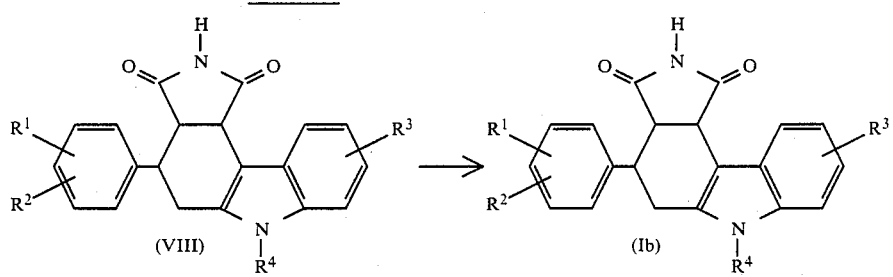

(C) Lactams of formula I, in which either A and B or C and D are hydrogen and the other two residues together form a carbonyl oxygen atom (compounds Ic), are prepared by reduction of imides of formulae IA or Ib in which not only A and B but also C and D form a carbonyl oxygen atom, according to Scheme III below. Preferred reducing agents used: zinc amalgam/gaseous hydrogen chloride in Cl–C4 alcohols, zinc amalgam in glacial acetic acid or zinc in glacial acetic acid. Regioisomeric mixtures of compounds Ic can be separated by usual processes, such as crystallization or chromatography. Preferably the carbonyl oxygen atom formed by C and D is reduced under the disclosed reaction conditions, see Scheme III below.

Scheme III

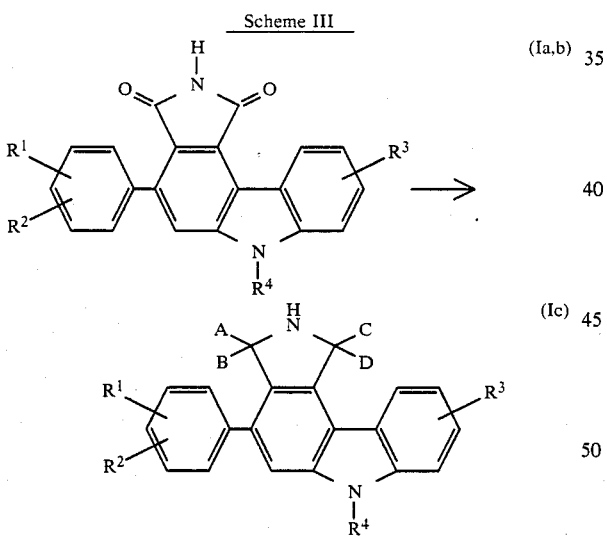

(D) Hydroxylactams of formula I, in which either A and B or C and D to together form a carbonyl oxygen atom, one of the two other residues is hydrogen and the other is hydroxyl (compounds Id), are prepared according to Reaction Scheme IV below also by reduction of imides of the formulae Ia or Ib. Preferred reducing agents are zinc amalgam/gaseous hydrogen chloride in Cl–C4 alcohols at temperatures below 20° C. or borohydrides, such as e.g. sodium borohydride, preferably in Cl–C4 alcohols or alcohol/water mixtures or lithium aluminum hydride in an aprotic solvent Regioisomeric mixtures of compounds Id can be separated by usual processes of crystallization or chromatography, see Scheme IV below.

Scheme IV

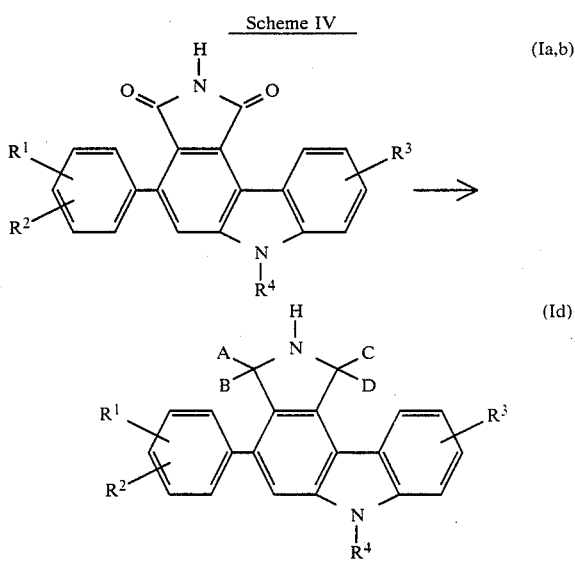

(E) Lactams of formula Ic, in which $R^4$ is hydrogen (compound Ic'), can be alkylated in a known manner on the indole nitrogen atom to lactams of formula Ic'' by reaction with compounds $R^{4'}$-X, in which $R^{4'}$ possesses the meanings given for $R^4$ with the exception of hydrogen and X preferably stands for halogen, especially iodine, bromine or chlorine, according to Scheme V in the presence of bases, such as hydrides, carbonates, hydroxides, oxides, or alkoxides of the alkali or alkaline earth metals, or of organo-lithium compounds. The described process of the alkylation of the compounds of Ic' is surprising since it was not foreseen that the introduction of the residue $R^{4'}$ takes place selectively on the indole nitrogen atom and not on the nitrogen atom of the lactam ring, see Scheme V below.

Scheme V

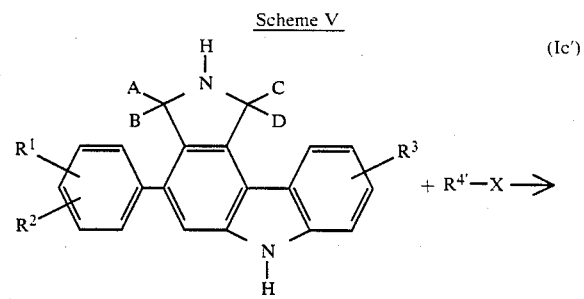

-continued
Scheme V

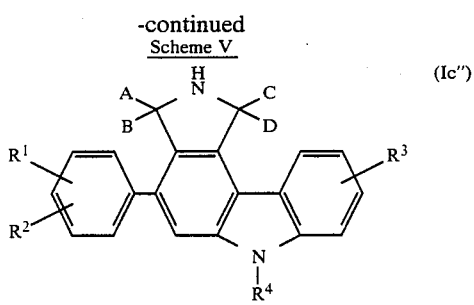

(Ic'')

(F) Compounds of formula I, in which $R^1$ and/or $R^2$ and/or $R^3$ is hydroxyl, can also be prepared in a known manner by ether fission of compounds of the general formula I, in which $R^1$ and/or $R^2$ and/or $R^3$ are alkoxy of from one to four carbon atoms.

Compounds of formula I, in which $R^1$ and/or $R^2$ and/or $R^3$ are unsubstituted amino group, can also be prepared in a known manner by reduction of compounds of the formula I, in which $R^1$ and/or $R^2$ and/or $R^3$ are nitro.

Compounds of formula I, in which $R^1$ and/or $R^2$ and/or $R^3$ are unsubstituted amino groups, can also be prepared in a known manner by aminoalkylation of compounds of formula I, in which $R^1$ and/or $R^2$ and/or $R^3$ are hydroxyl. The aminoalkyl radicals used correspond to those which are defined in the following paragraph as especially suitable for $R^4$.

Unsubstituted and substituted aminoalky groups with up to 12 carbon atoms especially suitable for $R^4$ are unsubstituted aminoalkyl groups, such as 2-aminoethyl, a 3-aminopropyl, or a 1-amino-2-propyl radical, N,N-dialkylaminoalkyl or N,N-alkylbenzylaminoalkyl groups with C1-C4-alkyl substituents on the nitrogen atoms and one to four carbon atoms in the alkyl chain, whereby the alkyl chain can be substituted by further C1-C4 alkyl radicals, a hydroxyl or a methoxy group, especially a 2-dimethylaminoethyl, 3-dimethylamino-1-propyl, 3-dimethylamino-2-propyl, 2-diethylaminoethyl, 2-[N-benzyl-N-methylamino]-ethyl, 3-N-benzyl-N-methyamino]-propyl, 3-dimethylamino-2-hydroxy-1-propyl, 3-diethylamino-2-hydroxy-1-propyl, 2-piperidinoethyl, 3-piperidinopropy], 2-pyrrolidinoethyl, 3-pyrrolidinopropyl, 2-morpholinoethyl, 3-morpholinopropyl, piperidin-2-ylmethyl, N-methylpiperidin-2-ylmethyl, 3-dimethylamino-2-methoxy-1-propyl, 3-diethylamino-2-methoxy-1-propyl, pyrrolidin-2-ylmethyl or an N-methylpyrrolidin-2-ylmethyl group. Further residues especially suitable for $R^4$ are straight-chained or branched alkyl groups with one to four carbon atoms, especially methyl, ethyl, n-propyl, isopropyl and n-butyl, cyanoalky groups with two or three carbon atoms, preferred cyanomethyl and 2-cyanoethy, alkoxycarbonylalkyl groups with up to seven carbon atoms, preferred 2-methoxycarbonylethyl, 2-ethoxycarbonylethyl, and methoxycarbonylmethyl.

Preferred residue combinations for $R^1$ and $R^2$ are: $R^1$ and $R^2$ hydrogen or $R^1$ hydrogen and $R^2$ a 2-methyl, 2-chloro, 3-chloro, 4-chloro, 2-bromo, 2-methoxy, 2-fluoro, 2-trifluoromethyl, 3-methoxy, 4-methoxy, 2-amino, 2-nitro, 2-hydroxy, or 2-(3-dimethylaminopropoxy) group or $R^1$ a 2-nitro group and $R^2$ a 5-methoxy group.

Lactams or hydroxylactams of formula I, in which the residues A and B are different from the residues C and D, can also be used as regioisomeric mixtures or, as described above, separated by known processes, such as crystallization or chromatography.

Hydroxylactams of formula I, in which one of the residues A, B, C or D is hydroxyl and is bound to a chiral center, or compounds of formula I which have a chiral center in the residues $R^1$, $R^2$, $R^3$ or $R^4$, can be used as stereoisomeric mixtures or in the form of enantiomers. The enantiomers can be obtained according to the processes usually employed for optical separations of stereoisomers.

Basic compounds of formula I which have a basic center on $R^1$, $R^2$, $R^3$ or $R^4$ are, for the purpose of purification and for galenical reasons, preferably converted into crystalline, pharmacologically acceptable salts. The salts are obtained in the usual way by neutralization of the bases with corresponding inorganic or organic acids. Acids include but are not limited to hydrochloric acid, sulphuric acid, phosphoric acid, hydrobromic acid, acetic acid, tartaric acid, lactic acid, citric acid, malic acid, salicylic acid, ascorbic acid, malonic acid, fumaric acid, oxalic acid or succinic acid. The acid-addition salts are, as a rule, obtained in a known manner by mixing of the free base or its solutions with the corresponding acid or its solution in an organic solvent, for example, a lower alcohol, such as methanol, ethanol or 2-propanol, or a lower ketone, such as acetone or 2-butanone, or an ether, such as diethyl ether, diisopropyl ether, tetrahydrofuran or dioxan.

Compounds of the present invention are potent inhibitors of protein kinases, such as protein kinase C. Thus, e.g. the compound of Example 2a shows, in the enzyme assay of protein kinase C activated with phosphatidylserine and iacylglycerol, a 50% inhibition at a concentration of 0.58 $\mu$mole/1. The experiment was carried out according to EP-OS 0 255 126 (inhibition of protein kinase C).

Protein kinase C plays an important key role for the intracellular signal transduction and is closely linked with the regulation of contractile, secretory, and proliferative processes. On the basis of these properties, the compounds according to the present invention are useful for the prevention and/or treatment of heart and blood vessel diseases, such as thromboses, arterioscleroses, hypertension, of inflammatory processes, allergies, cancers, and certain degenerative damages of the central nervous system as well as for the treatment of viral diseases. The compounds can be administered in the particular suitable formulation enterally or parenterally in doses of 1 to 500 mg/kg, preferably 1 to 50 mg/kg.

The compounds according to the present invention can be administered orally or parenterally in liquid or solid form. As injection solution, water which contains the additives usual in the case of injection solutions, such as stabilizing agents, solubilizing agents, or buffers is used.

Such additives are e.g. tartrate and citrate buffers, ethanol, complex formers (such as ethylenediamine-tetraacetic acid and its nontoxic salts), as well as high molecular polymers (such as liquid polyethylene oxide) for viscosity regulation. Solid carrier materials are e.g. starch, lactose, mannitol, methylcellulose, talc, highly dispersed silicic acids, high molecular fatty acids (such as stearic acid), gelatine, agar-agar, calcium phosphate, magnesium stearate, animal and vegetable fats, solid high molecular polymers (such as polyethylene glycol); compositions suitable for oral administration can, if desired, contain additional flavoring and/or sweetening materials.

The following examples are illustrative of the present invention but are not meant to limit the scope in any way.

Example 1 (according to Process A) 1,2,3,6-Tetrahydro-1,3-dioxo-4-phenylpyrrolo[3,4-c]carbazole 3.5 g (10.2 mmole) 1,3-dihydro-4-(2-nitrophenyl)-1,3-dioxo-7-phenyl-2H-isoindole and 9.5 g (36.2 mmole) triphenylphosphine are heated under reflux for 16 hours in 100 ml 2,4,6-collidine. The solvent is distilled off in a vacuum and the residue chromatographed on silica gel with toluene/ethyl acetate 3:1. The fraction with the Rf 0.3 is isolated and recrystallized from cyclohexane/acetone. One obtains 1,2,3,6-tetrahydro-1,3-dioxo-4-phenylpyrrolo[3,4-c]carbazole in the form of yellow crystals of the mp 262°–264° C.

The 1,3-dihydro-4-(2-nitrophenyl)-1,3-dioxo-7-phenyl-2H-isoindole used as starting product is prepared as follows:

5.5 g (15.8 mmole) 1,3,3a,4,7,7a-hexahydro-4-(2-nitrophenyl)-1,3-dioxo-7-phenyl-2H-isoindole and 9.1 g (40.1 mmole) 2,3-dichloro-5,6-dicyano-p-benzoquinone (DDQ) are heated under reflux for 16 hours in 100 ml t-butylbenzene. The solvent is removed in a vacuum and the residue chromatographed on silica gel with toluene/ethyl acetate 3:1. The fraction with the $R_f$ of 0.4 is isolated, stirred with a little hot ethanol, and the crystals formed after cooling are filtered off. After recrystallization from ethyl acetate, one obtains 1,3-dihydro-4-(2-nitrophenyl)-1,3-dioxo-7-phenyl-2H-isoindole in the form of colorless crystals of the mp 224°–226° C.

The 1,3,3a,4,7,7a-hexahydro-4-(2-nitrophenyl)-1,3-dioxo-7-phenyl-2H-isoindole used as starting product is prepared as follows:

7.5 g (29.8 mmole) (E,E)-1-(2-nitrophenyl)-4-phenyl-1,3-butadiene and 2.9 g (29.9 mmole) maleic acid imide are heated in 10 ml toluene to 130° C. for 12 hours. After addition of 1.5 g (15.5 mmole) maleic acid imide it is heated at 130° C. for a further 24 hours. After cooling, it is diluted with 40 ml dichloromethane, the product filtered off, and crystallized from ethanol. One obtains 1,3,3a,4,7,7a-hexahydro-4-(2-nitrophenyl)-1,3-dioxo-7-phenyl-2H-isoindole in the form of pale yellow crystals, which decompose from 200°–208° C.

The (E,E)-1-(2-nitrophenyl)-4-phenyl-1,3-butadiene used as starting product is obtained in analogy to *Tetrahydron Lett,* 1983, 1441 by isomerization with iodine in toluene of the (E,E)- and (E,Z)- isomer mixture formed by the reaction of 2-nitrobenzyl-triphenylphosphoniumbromide with transcinnamaldehyde.

The following compound is obtained in an analogous way:

EXAMPLE 1a 1,2,3,6-Tetrahydro-4-(2-methoxyphenyl)-1,3-dioxopyrrolo[3,4-c]carbazole, mp 300° C (decomp.) from toluene (starting from 2-nitrobenzyltriphenylphosphonium bromide and 2-methoxycinnamaldehyde).

Example 1 (according to Process B) 1,2,3,6-Tetrahydro-1,3-dioxo-4-phenylpyrrolo[3,4-c]carbazole 1.2 g (3.8 mmole) 1,2,3,3a,4,5,6,10c-octahydro-1,3-dioxo-4-phenylpyrrolo[3,4-c]carbazole and 2.2 g (9.7 mmole) DDQ are heated under reflux for 20 hours in 30 ml toluene. The solvent is distilled off in a vacuum and the residue chromatographed on silica gel with toluene-/ethyl acetate 3:1. The fraction with the $R_f$ of 0.3 is isolated, stirred up with acetone/diisopropyl ether, and the crystals formed are filtered off. One obtains 1,2,3,6-tetrahydro-1,3-dioxo-4-phenyl-pyrrolo[3,4-c]carbazole in the form of yellow crystals of the mp 262°–263° C.

The 1,2,3,3a,4,5,6,10c-octahydro-1,3-dioxo-4-phenyl-pyrrolo[3,4-c]carbazole used as starting product is prepared as follows:

1.3 g (5.9 mmole) (E)-1-(2-indolyl)-2-phenylethylene and 0.7 g (7.2 mmole) maleic acid imide are heated under reflux for 16 hours in 25 ml toluene. After the addition of 0.1 g (1 mmole) maleic acid imide, it is refluxed for a further 8 hours After cooling, the crystals formed are filtered off and chromatographed on silica gel with toluene/ethyl acetate 4:1. The fraction with the $R_f$ of 0.1 is isolated and recrystallized from toluene. One obtains 1,2,3,3a,4,5,6,10c-octahydro-1,3-dioxo-4-phenylpyrrolo3,4-c]carbazole in the form of colorless crystals of the mp 212°–215° C.

The (E)-1-(2-indolyl)-2-phenylethylene used as starting product is prepared as follows:

2.0 g (13.7 mmole) 2-indolealdehyde and 5.3 g (13.7 mmole) benzyltriphenylphosphonium chloride are heated to a boil in 30 ml dry ethanol. A freshly prepared solution of 0.32 g (13.9 mmole) sodium in 15 ml ethanol is added dropwise thereto within about 1.5 hours. Subsequently, it is boiled under reflux for one hour, after cooling the solvent is distilled off, and the residue is partitioned between dichloromethane and water. The organic phase is dried over sodium sulphate, evaporated, and the residue chromatographed o silica gel with cyclohexane/toluene 7:3. The fraction with the $R_f$ of 0.4 is isolated. One obtains (Z)-1-(2-indolyl)-2-phenylethylene in the form of a pale yellow oil which, in the case of drying in a vacuum, crystallizes. The fraction with the $R_f$ of 0.2 is evaporated, the residue stirred with cyclohexane, and the crystals formed are filtered off. One obtains (E)-1-(2-indolyl)-2-phenylethylene in the form of almost colorless crystals of the mp 205°–206° C. The preparation of the 2-indolealdehyde takes place according to the statements in the literature (*Arch Pharm* 310, 975, 1977) from 2-indolecarboxylic acid esters.

ln an analogous way, the following examples are obtained:

Insofar as these are substituted on the carbazole nitrogen atom, the corresponding residue $R^4$ was already introduced by alkylation of the corresponding 2-indolecarboxylic acid ester according to known processes of N-alkylating indoles (e.g., analogously to *Synthesis,* 1976, 124).

EXAMPLE 2

6-Ethyl-1,2,3,6-tetrahydro-1,3-dioxo-4-phenylpyrrolo[3,4-c]carbazole, mp 272°–277° C. from toluene.

EXAMPLE 2a 4-(2-Chlorophenyl)-6-ethyl-1,2,3,6-tetrahydro-1,3-dioxopyrrolo[3,4-c]carbazole, mp 272°–274° C. from toluene.

EXAMPLE 2b 4-(4-Chlorophenyl)-6-ethyl-1,2,3,6-tetrahydro-1,3-dioxopyrrolo[3,4-c]carbazole, mp 300° C. from toluene.

EXAMPLE 2c 4-(3-Chlorophenyl)-6-ethyl-1,2,3,6-tetrahydro-1,3-dioxopyrrolo[3,4-c]carbazole, mp 298°–299° C. from toluene/diisopropyl ether.

EXAMPLE 2d 4-(2-Chlorophenyl)-1,2,3,6-tetrahydro-6-methyl-1,3-dioxopyrrolo[3,4-c]carbazole, mp 250°–255° C. (decomp.) from diisopropyl ether.

EXAMPLE 2e 1,2,3,6-Tetrahydro-6-methyl-4-phenyl-1,3-dioxopyrrolo-[3,4]carbazole, mp 312°–314° C. from diisopropyl ether.

EXAMPLE 2f 4-(2-Chlorophenyl)-1,2,3,6-tetrahydro-1,3-dioxopyrrolo[3,4-c]carbazole, mp 310°–313° C. from ethanol.

EXAMPLE 2g 1,2,3,6-Tetrahydro-4-(2-nitrophenyl)-1,3-dioxopyrrolo[3,4-c]carbazole, mp 310°–312° C. from ethanol.

EXAMPLE 2h 4-(4-Chlorophenyl)-1,2,3,6-tetrahydro-6-methyl-1,3-dioxopyrrolo[3,4-c]carbazole, mp 332°–337° C. from ethanol.

EXAMPLE 2i 4-(3-Chlorophenyl)-1,2,3,6-tetrahydro-6-methyl-1,3-dioxopyrrolo[3,4-c]carbazole, mp 299°–302° C. from ethanol.

EXAMPLE 2j 4-(2-Trifluoromethylphenyl-1,2,3,6-tetrahydro-6-methyl-1,3-dioxo-pyrrolo3,4-c]carbazole, mp 310°–312° C. from dichloromethan.

Example 3 (according to Process C) 1,2,3,6-Tetrahydro-4-(2-methoxyphenyl)-3-oxopyrrolo[3,4-c]carbazole 5 g (76 mmole) zinc powder and 0.5 g (1.8 mmole) mercury (II) chloride in 5 ml water are stirred for 20 minutes at 20° C, then 0.15 ml concentrated hydrochloric acid added thereto and further stirred for one minute. Immediately thereafter, the zinc powder is first washed with water, then with ethanol, and finally with dry ethanol. The zinc powder is suspended in 100 ml dry ethanol. While stirring, 1.2 g (3.5 mmole) 1,2,3,6-tetrahydro-4-(2-methoxy)phenyl-1,3-dioxopyrrolo[3,4-c]carbazole (Example 1a) are added thereto and it is heated for 3 hours under reflux with slowpassing through of dry hydrogen chloride. After cooling, it is evaporated and the residue partitioned between potassium carbonate solution and ethyl acetate. The aqueous phase is again extracted with ethyl acetate, the combined organic phases dried over sodium sulphate, and evaporated. The residue is chromatographed on silica gel with toluene/ethyl acetate 1:1, the fraction with the $R_f$ of 0.15 is isolated, stirred with toluene/ethanol 9:1, and the crystals formed are filtered off. One obtains 1,2,3,6-tetrahydro-4-(2-methoxyphenyl)-3-oxopyrrolo[3,4-c]-carbazole in the form of pale yellow crystals which decompose between 265° and 268° C.

The following compounds are obtained in an analogous way:

EXAMPLE 3a 1,2,3,6-Tetrahydro-3-oxo-4-phenylpyrrolo[3,4-c]carbazole, mp 250° C. (decomp.) from diisopropyl ether (prepared from Example 1)

EXAMPLE 3b 4-(2-Chlorophenyl)-6-ethyl-1,2,3,6-tetrahydro-3-oxopyrrolo[3,4-carbazole, mp 265°–275° C. (decomp.) from diisopropylether (prepared from Example 2a).

Example 4 (according to Process D) 4-(2-Chlorophenyl)-6-ethyl-1,2,3,6-tetrahydro-1-hydroxy-3-oxopyrrolo3,4-c]carbazole (Example 4a) and 4-(2-chlorophenhl)-6-ethyl-1,2,3,6-tetrahydro-3-hydroxy-1-oxopyrrolo[3,4-c]carbazole (Example 4b).

0.3 g (2.13 mmole) 4-(2-chlorophenyl)-6-ethyl-1,2,3,6-tetrahydro-1,3-dioxopyrrolo[3,4-c]carbazole (Example 2a) are suspended in 20 ml 90% methanol, a solution of 0.16 g (4.23 mmole) sodium borohydride in 5 ml methanol added dropwise thereto with vigorous stirring and stirred for 5 days at room temperature. The excess sodium borohydride is decomposed with acetic acid, the solvent is distilled off, and the crystalline residue is chromatographed on silica gel with toluene/ethyl acetate 1:1. The fraction with the $R_f$ of 0.3 is isolated, stirred up with toluene/diisopropyl ether, and the crystals formed are filtered off. One obtains 4-(2-chlorophenyl)-6-ethyl-1,2,3,6-tetrahydro-1-hydroxy-3-oxopyrrolo[3,4-c]carbazole (Example 4a) in the form of pale beige crystals of the mp 225°–228° C.

The fraction with the $R_f$ of 0.25 (toluene/ethyl acetate 1:1) is isolated, stirred up with diisopropyl ether, and the crystals formed are filtered off. One obtains 4-(2-chlorophenyl)-6-ethyl-1,2,3,6-tetrahydro3-hydroxy-1-oxopyrrolo[3,4-c]carbazole (Example 4b) in the form of colorless crystals of the mp 232°–236° C.

EXAMPLE 5

1,2,3,6-Tetrahydro-4-(2-hydroxyphenyl)-3-oxopyrrolo[3,4-c]carbazole

To 212 mg (0.65 mmole) 1,2,3,6-tetrahydro-4-(2-methoxyphenyl)-3-oxopyrrolo[3,4-c]carbazole in 25 ml dry dichloromethane is added dropwise at −78° C. a solution of 0.1 ml (1.06 mmole) boron tribromide in 2 ml dichloromethane. After 1 hour at −78° C., it is warmed to room temperature and stirred for a further 1.5 hours at room temperature. It is cooled to −10° C. and 10 ml water added dropwise thereto. After warming to room temperature, it is diluted with ethyl acetate and the precipitate insoluble in both phases is filtered off. The organic phase of the filtrate is separated off, dried over sodium sulphate, and evaporated. The residue, together with the filtered off insoluble precipitate is boiled out with ethyl acetate. After cooling, the crystals are filtered off. One obtains 1,2,3,6-tetrahydro-4-(2-hydroxyphenyl)-3-oxopyrrolo[3,4-c]carbazole in the form of pale beige crystals of the mp >300° C. (decomp.).

EXAMPLE 6

4-[2-(3-Dimethylaminopropoxy)-phenyl]-7-)3-dimethylaminoporpyl)-1,2,3,6-tetrahydro-3-oxopyrrolo[3,4-c]carbazole dihydrochloride 98 mg (0.31 mmole) 1,2,3,6-tetrahydro-4-(2-hydroxyphenyl)-3-oxopyrrolo[3,4-c]carbazole (Example 5) are heated under reflux for 72 hours with 80 mg (0.66 mmole) 3-dimethylaminopropyl chloride, 91 mg (0.66 mmole) potassium carbonate and a spatula tip of potassium iodide in 25 ml acetone. After cooling, it is evaporated and the residue partitioned between water and ethyl acetate. The organic phase is separated off, dried over sodium sulphate, and the residue obtained after evaporation chromatographed on silica gel with NH$_3$-saturated dichloromethane/methanol 9:1. The fraction with the R*f* of 0.6 is isolated, dissolved in an ether/ethyl acetate mixture, and the dihydrochloride precipitated with hydrogen chloride in ether. One obtains 4-[2-(3-dimethylaminopropoxy)phenyl]-6-(3-dimethylaminopropyl)-1,2,3,6-tetrahydro-3-oxopyrrolo[3,4-c]carbazole dihydrochloride in the form of beige crystals which decompose above 170° C.

EXAMPLE 7

4-(2-Aminophenyl)-1,2,3,6-tetrahydro-1,3-dioxopyrrolo[3,4-c]carbazole 0.5 g (1.51 mmole) 1,2,3,6-tetrahydro-4-(2-nitrophenyl)-1,3-dioxopyrrolo[3,4-c]carbazole (Example 2g) in 30 ml dimethylformamide are hydrogenated at room temperature with 0.27 g palladium on active charcoal (10%). After 4 hours, the catalyst is filtered off and the solution evaporated in a vacuum. The residue is stirred up with ethyl acetate, the crystals filtered off, and recrystallized from methanol. One obtains 4-(2-aminophenyl)-1,2,3,6-tetrahydro-1,3-dioxopyrrolo[3,4-c]carbazole in the form of yellow crystals of the mp >300° C.

Example 8 (according to Process D)

4-(4-Chlorophenyl)-6-ethyl-1,2,3,6-tetrahydro-1-hydroxy-3-oxopyrrolo[3,4-c]carbazole (Example 8a) and 4-(4-chlorophenyl)-6-ethyl-1,2,3,6-tetrahydro-3-hydroxy-1-oxopyrrolo[3,4-c]carbazole (Example 8b)

A solution of 0.48 g (1.28 mmole) 4-(4-chlorophenyl)-6-ethyl-1,2,3,6-tetrahydro-1,3-dioxopyrrolo[3,4-c]carbazole (Example 2b) in 35 ml dry tetrahydrofuran is added dropwise at 20° C. to a suspension of 0.097 g (2.56 mmole) lithium aluminum hydride in 10 ml tetrahydrofuran and stirred for 16 hours at room temperature. The excess lithium aluminum hydride is decomposed with ethanol and water and the precipitate obtained is filtered off. The filtrate is evaporated and the residue chromatographed on silica gel with toluene/ethyl acetate 1:1. The fraction with the R*f* of 0.35 is isolated, stirred with toluene/ethyl acetate, and the crystals filtered off. One obtains 4-(4-chlorophenyl)-6-ethyl-1,2,3,6-tetrahydro-3-hydroxy-1-oxopyrrolo3,4-c]carbazole (Example 8b) in the form of yellow crystals of the mp 230° C. (decomp.).

The fraction with the R*f* of 0.25 is isolated, stirred with toluene/ethyl acetate, and the crystals filtered off. One obtains 4-(4-chlorophenyl)-6-ethyl-1,2,3,6-tetrahydro-1-hydroxy-3-oxopyrrolo[3,4-c]carbazole (Example 8a) in the form of pale yellow crystals of the mp >250° C. (decomp.).

EXAMPLE 9

6-(3-Dimethylaminopropyl)-1,2,3,6-tetrahydro-1,3-dioxo-4-phenyl-pyrrolo[3,4-c]carbazole To 5.89 g (14.7 mmole) 6-(3-dimethylaminopropyl)-1,2,3,3a,4,5,6,10c-octahydro-1,3-dioxo-4-phenylpyrrolo[3,4-c]carbazole in 150 ml glacial acetic acid are added 3.0 g (43.5 mmole) sodium nitrite under ice cooling, stirring and passing through nitrogen. The dark red solution is stirred for 12 hours at 20° C. The solvent is distilled off under vacuum and the residue partitioned between ethyl acetate (1.2 1) and saturated sodium hydrogen carbonate solution (200 ml). The ethyl acetate phase is separated, washed with water, dried (sodium sulphate), and evaporated. The residue is chromatographed on silica gel with dichloromethane/methanol 9:1. The fraction with R*f* 0.3 is isolated and stirred up with diisopropyl ether/ethyl acetate. The crystals formed are filtered off. One obtains 6-(3-dimkethylaminopropyl)-1,2,3,6-tetrahydro- 1,3-dioxo-4-phenyl-pyrrolo[3,4-c]carbazole in the form of yellow crystals, mp ca. 200° C.

The 6-(3-dimethylaminopropyl)-1,2,3,3a,4,5,6,10c-octahydro-1,3-dioxo-4-phenyl-pyrrolo[3,4-c]carbazole used as starting product is prepared by reacting (E)-1-[1-(3-dimethylaminopropyl)-2-indolyl]-2-phenylethylene with maleinimide in toluene analog to Example 1, Process B.

(E)-1-[1-(3-Dimethylaminopropyl)-2-indolyl]-2-phenylethylene is prepared as follows:

11.8 g (53.8 mmole) (E)-1-(-2-indolyl)-2-phenylethylene (preparation see Example 1, Process B or Can J Chem, 1973, 51, 792) and 8.5 g (69.9 mmole) 3-dimethylaminopropylchloride with 9.7 9 (70 mmole) potassium carbonate and a spatula tip of potassium iodide in 300 ml acetone are boiled under reflux for 64 hours. The solvent is distilled off and the residue partitioned between ethyl acetate (300 ml) and water (100 ml). The ethyl acetate phase is separated, dried (sodium sulphate), and evaporated. The residue is separated on silica gel with dichloromethane/methanol 95:5. The fraction with R*f* 0.15 is isolated.

One obtains (E)-1-[1-(3-dimethylaminopropyl)-2-indolyl]-2-phenylethylen in the form of a yellow oil.

In an analogous manner the following compounds are obtained:

EXAMPLE 9a 4-(2-Chlorophenyl)-1,2,3,6-tetrahydro-6-(2-morpholinoethyl)-1,3-dioxo-pyrrolo[3,4-c]carbazole, mp 225°–228° C. from ethyl acetate.

EXAMPLE 9b 4-(2-Chlorophenyl)-6-(2-diethylaminoethyl)-1,2,3,6-tetrahydro-1,3-dioxo-pyrrolo[3,4-c]carbazole, mp 196°–200° C. from toluene.

EXAMPLE 9c 4-(2-Chlorophenyl)-6-(3-dimethylaminopropyl)-1,2,3,6-tetrahydro-1,3-dioxo-pyrrolo3,4-c]carbazole, mp 208°–211° C. from diisopropyl ether/ethyl acetate.

EXAMPLE 9d 6-(3-Dimethylaminopropyl)-1,2,3,6-tetrahydro-1,3-dioxo-4-(2-trifluoromethylphenyl)-pyrrolo[3,4-c]carbazole, mp 195°–197° C. from diisopropyl ether.

EXAMPLE 9e 4-(2-Chlorophenyl)-6-(3-dimethylamino-2-methoxy-1-propyl)-1,2,3,6-tetrahydro-1,3-dioxo-pyrrolo3,4-c]carbazole, mp 222°–225° C. from ethyl acetate.

EXAMPLE 9f 4-(2-Chlorophenyl)-l,2,3,6-tetrahydro-l,3-dioxo-6-(2-pyrrolidinoethyl)-pyrrolo[3,4-c]carbazole, mp 226°–230° C. from diisopropyl ether.

EXAMPLE 9g 6-(3-Dimethylaminopropyl)-1,2,3,6-tetrahydro-4-(2-methylphenyl)-1,3-dioxo-pyrrolo[3,4-c]carbazole, mp 182°–185° C. from diisopropyl ether/ethyl acetate.

EXAMPLE 9h 6-(3-Dimethylaminopropyl)-4-(2-fluorophenyl)-1,2,3,6-tetrahydro-1,3-dioxo-pyrrolo[3,4-c]carbazole, mp 202°–206° C. from diisopropyl ether/ethyl acetate.

EXAMPLE 9i 6-(3-Diethylamino-2-hydroxy-1-propyl)-1,2,3,6-tetrahydro-1,3-dioxo-4-phenyl-pyrrolo[3,4-c]carbazole, mp >190° C. dec. from diisopropyl ether.

EXAMPLE 10

6-(2-Cyanoethyl)-1,2,3,6-tetrahydro-4-(2-methylphenyl)-1,3-dioxo-pyrrolo[3,4-c]carbazole 200 mg (0.52 mmole) 6-(2-cyanoethyl)1,2,3-,3a,4,5,6,10c-octahydro-4-(2-methylpheny)-1,3-dioxo-pyrrolo[3,4-c]carbazole and 34 mg (1.06 mmole) sulfur in 25 ml trielhylene glycol dimethyl ether are heated for 1 hour to 220° C. After cooling 50 ml water is added under stirring and the precipitated crude product is filtered off. The crude product is dissolved in tetrahydrofuran; the tetrahydrofuran solution is then washed with saturated sodium chloride solution, dried (sodium sulphate), and evaporated. The residue is chromatographed on silica gel with dichloromethane/methanol 95:5 and the fraction with $R_f 0.5$ is isolated.

One obtains 6-(2-cyanoethyl)-1,2,3,6-tetrahydro-4-(2-methylphenyl)-1,3-dioxo-pyrrolo[3,4-c]carbazole in the form of yellow crystals which decompose over ca. 300° C.

The 6-(2-cyanoethyl)-1,2,3,3a,4,5,6,10c-octahydro-4-(2-methylphenyl)-1,3-dioxo-pyrroo[3,4-c]carbazole used as starting material is prepared by reacting (E)-1-[1-(2-cyanoethyl)-2-indolyl]-2-(2-methylphenyl)ethylen with maleinimide in toluene analogous to Example 1, Process B.

(E)-1-[1-(2-Cyanoethyl)-2-indolyl]-2-(2-methylphenyl)ethylen is prepared as follows:

To 600 mg (2.74 mmole) (E)-1-(-2-indolyl)-2-(2-methylphenyl)ethylen (prepared analogous to Example 1, Process B or *Can J Chem*, 1973, 51, 792) and 1.02 g (19.2 mmole) acrylonitrile in 30 ml acetonitrile are added two drips 1,8-diazabicyclo[5.4.o]undec-7-en (DBU) and the mixture is stirred for 48 hours at 20° C. The solvent is evaporated and the oily residue is crystallized from diisopropyl ether/ethyl acetate (20:1).

One obtains (E)-1-[1-(2-cyanoethyl)-2-indolyl]-2-(2-methylphenyl)-ethylen in the form of pale yellow crystals.

In an analogous manner the following compounds are obtained:

EXAMPLE 10a 6-(2-Cyanoethyl)-1,2,3,6-tetrahydro-1,3-dioxo-4-phenyl-pyrrolo[3,4-c]carbazole, mp decomp. over 300° C., from diisopropyl ether.

EXAMPLE 10b 6-(2-Cyanoethyl)-4-(2-fluorophenyl)-1,2,3,6-tetrahydro-1,3-dioxo-pyrrolo[3,4-c]carbazole, mp decomp. over 300° C., from dichloromethane/methanol.

We claim:
1. A compound of formula

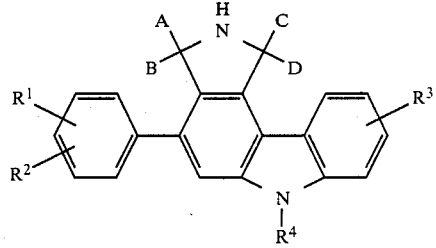

or a pharmaceutically acceptable salt thereof wherein A and B or C and D are the same and are hydrogen or together form a carbonyl oxygen or are different and one of A and B or of C and D is hydrogen and the other is hydroxyl with the proviso that at least one of A and B or C and D together form a carbonyl oxygen;

$R^1$, $R^2$, and $R^3$ are each independently hydrogen; halogen; trifluoromethyl; alkyl of from one to four carbon atoms; nitro; amino which is unsubstituted or substituted by alkyl of from one to four carbon atoms; benzyl; alkoxy of from one to four carbon atoms, hydroxy, acyl of from one to four carbon atoms; aminoalkoxy of from one to 12 carbon atoms unsubstituted or substituted on the alkyl chain by alkyl of from one to four carbon atoms, hydroxyl, alkoxy of from one to four carbon atoms, or the aminoalkoxy is substituted on the nitro9en atom by alkyl of from one to four carbon atoms or benzyl or the aminoalkoxy is substituted by two substituents on the nitrogen or by one substituent on the nitrogen and one on the alkyl chain wherein the substituents together with the nitrogen to which they are attached form a heterocyclic ring of from three to six carbon atoms or a heterocyclic ring with oxygen, sulfur, and/or another nitrogen, the heterocyclic ring is unsubstituted or substituted by alkyl of from one to four carbon atoms; and $R^4$ is hydrogen, straight or branched alkyl of from one to six carbon atoms, cyanoalkyl of from two to four carbon atoms, alkoxycarbonylalkyl of from three to seven carbon atoms, aminoalkyl unsubstituted or substituted in the alkyl chain by: alkyl of from one to four carbon atoms, hydroxyl, alkoxy of from one to four carbon atoms or substituted on the nitrogen by alkyl of from one to four carbon atoms or benzyl or substituted by two substituents on the nitrogen or by one substituent on the nitrogen and one substituent on the alkyl chain which together with the nitrogen atom form a heterocyclic ring of from three to six carbon atoms or a heterocyclic ring which contains oxygen, sulfur, and/or another nitrogen, the heterocyclic ring is unsubstituted or substituted by alkyl of from one to four carbon atoms.

2. A compound according to claim 1 wherein $R^1$, $R^2$, and $R^3$ are the same or different and are hydrogen, fluorine, chlorine, bromine, trifluoromethyl, hydroxyl, nitro, methyl, ethyl, n-propyl, isopropyl, n-butyl, amino, methoxy, ethoxy, aminoethoxy, aminopropoxy, dimethylaminoethoxy, dimethylaminopropoxy, diethylaminoethoxy, N-benzyl-N-methylaminoethoxy, N-benzyl-N-methylaminopropoxy, dimethylaminohydroxypropoxy, piperidinoethoxy, piperidinopropoxy, pyrrolidinoethoxy, pyrrolidinopropoxy, morpholinoethoxy, morpholinopropoxy, pyrrolidnylmethoxy, piperidinylmethoxy, N-methylpiperidinylmethoxy, N- methylpyrrolidinylmethoxy, dimethylaminomethoxypropoxy, formyl, acetyl, propionyl or butyryl, and $R^4$ is hydrogen, methyl, ethyl, n-propyl, isopropyl, n-butyl, cyanomethyl, cyanoethyl, methoxycarbonylethyl, ethoxycarbonylethyl, methoxycarbonylmethyl, aminoethyl, aminopropyl, dimethylaminoethyl, dimethylaminopropyl, diethylaminoethyl, N-benzyl-N-methylaminoethyl, N-benzyl-N-methylaminopropyl, dimethylaminohydroxypropyl, diethylaminohydroxypropyl, piperidinoethyl, piperidinopropyl, pyrrolidinoethyl, pyrrolidinopropyl, morpholinoethyl, morpholinopropyl, pyrrolidinylmethyl, piperidinylmethyl, N-methylpiperidinylmethyl, dimethylaminomethoxypropyl, diethylaminomethoxypropyl, or N-methylpyrrolidinylmethyl.

3. A compound according to claim 2 wherein $R^1$ and $R^2$ are each independently hydrogen, 2-methyl, 2-chloro, 3-chloro, 4-chloro, 2-bromo, 2-methoxy, 3-methoxy, 4-methoxy, 2-fluoro, 2-trifluoromethyl, 2-amino, 2-nitro, 2-hydroxy, 2-(3-dimethylaminopropoxy) or $R^1$ is 2-nitro and $R^2$ is 5-methoxy and $R^4$ is 2-aminoethyl, 3-aminopropyl, 1-amino-2-propyl, 2-dimethyl-aminoethyl, 3-dimethylamino-1-propyl, 3-dimethylamino-2-propyl, 2-diethylaminoethyl, 2-[N-benzyl-N-methylamino]-ethyl, 3-[N-benzyl-N-methylamino]-propyl, 3-dimethylamino-2-hydroxy1-propyl, 3-diethylamino-2-hydroxy-1-propyl, 2-piperidinoethyl, 3-piperidinopropyl, 2-pyrrolidinoethyl, 3-pyrrolidinopropyl, 2-morpholinoethyl, 3-morpholinopropyl, piperidin-2-ylmethyl, N-methylpiperidin-2-ylmethyl, 3-dimethylamino-2-methoxy-1-propyl, 3-diethylamino-2-methoxy-1-propyl, pyrrolidin-2-ylmethyl, N-methylpyrrolidin-2-ylmethyl, methyl, ethyl, n-propyl, isopropyl, n-butyl, cyanomethyl, 2-cyanoethyl, 2-methoxycarbonylethyl, 2-ethoxycarbonylethyl, and methoxycarbonylmethyl.

4. A compound according to claim 1 selected from the group consisting of:

1,2,3,6-tetrahydro-1,3-dioxo-4-phenylpyrrolo-3,4-c]carbazole, 1,2,3,6-tetrahydro-4-(2-methoxyphenyl)-1,3-dioxopyrrolo[3,4-c]carbazole, 6-ethyl-1,2,3,6-tetrahydro-1,3-dioxo-4-phenylpyrrolo[3,4-c]carbazole, 4-(2-chlorophenyl)-6-ethyl-1,2,3,6-tetrahydro-1,3-dioxopyrrolo[3,4-c]carbazole, 4-(4-chlorophenyl)-6-ethyl-1,2,3,6-tetrahydro-1,3-dioxopyrrolo[3,4-c]carbazole, 4-(3-chlorophenyl)-6-ethyl-1,2,3,6-tetrahydro-1,3-dioxopyrrolo[3,4-c]carbazole, 4-(2-chlorophenyl)-1,2,3,6-tetrahydro-6-methyl-1,3-dioxopyrrolo[3,4-c]carbazole, 1,2,3,6-tetrahydro-6-methyl-4-phenyl-1,3-dioxopyrrolo[3,4-c]carbazole, 4-(2-chorophenyl)-1,2,3,6-tetrahydro-1,3-dioxopyrrolo[3,4-c]carbazole, 1,2,3,6-tetrahydro-4-(2-nitrophenyl)-1,3-dioxopyrrolo[3,4-c]carbazole, 4-(4-chlorophenyl)-1,2,3,6-tetrahydro-6-methyl-1,3-dioxopyrrolo[3,4-c]carbazole, 4-(2S 4-(3-chlorophenyl)-1,2,3,6-tetrahydro-6-methyl-1,3-dioxopyrrolo[3,4-c]carbazole, 4-(2-trifluoromethylphenyl)-1,2,3,6-tetrahydro-methyl-1,3-dioxo-pyrrolo3,4-c]carbazole, 1,2,3,6-tetrahydro-4-(2-methoxy-phenyl)-3-oxopyrrolo-[3,4-c]carbazole, 1,2,3,6-tetrahydro-3-oxo-4-phenylpyrrolo3,4-c]carbazole, 4-(2-chlorophenyl)-6-ethyl-1,2,3,6-tetrahydro-1-oxopyrrolo[3,4-c]carbazole, 4-(2-chlorophenyl)-6-ethyl-1,2,3,6-tetrahydro-3-hydroxy-3-oxopyrrolo[3,4-c]carbazole, 4-(2-chlorophenyl)-6-ethyl-1,2,3,6-tetrahydro-3-hydroxy-1-oxopyrrolo[3,4-c]carbazole, 1,2,3,6-tetrahydro-4-(2-hydroxyphenyl)-3-oxopyrrolo[3,4-c]carbazole, 4-[2-(3-dimethylaminopropoxy)-phenyl]-6-(3-dimethylaminopropyl)-1,2,3,6-tetrahydro-3-oxopyrrolo[3,4-c]carbazole dihydrochloride, 4-(2 TM aminophenyl)-1,2,3,6-tetrahydro-1,3-dioxopyrrolo[3,4-c]carbazole, 4-(4-chlorophenyl)-6-ethyl-1,2,3,6-tetrahydro-1-hydroxy-3-oxopyrrolo[3,4-c]carbazole, 4-(4-chlorophenyl)-6-ethyl-1,2,3,6-tetrahydro-3-hydroxy-1-oxopyrrolo[3,4-c]carbazole, 6-(3-dimethylaminopropyl)-1,2,3,6-tetrahydro-1,3-dioxo-4-phenyl-pyrrolo[3,4-c]carbazole, 4-(2-chlorophenyl)-1,2,3,6-tetrahydro-6-(2-morpholinoethyl)-1,3-dioxo-pyrrolo[3,4-c]carbazole, 4-(2-chlorophenyl)-6-(2-diethylaminoethyl)-1,2,3,6-tetrahydro-1,3-dioxo-pyrrolo[3,4-c]carbazole, 4-(2-chlorophenyl)-6-(3-dimethylaminopropyl)-1,2,3,6-tetrahydro-1,3-dioxo-pyrrolo[3,4-c]carbazole, 6-(3-dimethylaminopropyl)-1,2,3,6-tetrahydro-1,3-dioxo-4-(2-trifluoromethylphenyl)-pyrrolo-3,4-c]carbazole, 4-(2-chlorophenyl)-6-(3-dimethylamino-2-methoxy-1-propy)-1,2,3,6-tetrahydro-1,3-dioxopyrrolo[3,4-c]carbazole, 4-(2-chlorophenyl)-1,2,3,6-tetrahydro-1,3-dioxo-6-(2-pyrrolidinoethyl)-pyrrolo[3,4-c]carbazole, 6-(3-dimethylaminopropyl)-1,2,3,6-tetrahydro-4-(2-methylphenyl)-1,3-dioxo-pyrrolo[3,4-c]carbazole, 6-(3-dimethylaminopropyl)-4-(2-fluorophenyl)-1,2,3,6-tetrahydro-1,3-dioxo-pyrrolo[3,4-c]carbazole, 6-(3-diethylamino-2-hydroxy-1-propyl)-1,2,3,6-tetrahydro-1,3-dioxo-4-phenyl-pyrrolo[3,4-c]carbazole, 6-(2-cyanoethyl)-1,2,3,6-tetrahydro-4-(2-methylphenyl)-1,3-dioxo-pyrrolo[3,4-c]carbazole, 6-(2-cyanoethyl)-1,2,3,6-tetrahydro-1,3-dioxo-4-phenylpyrrolo[3,4-c]carbazole, and 6-(2-cyanoethyl)-4-(2-fluorophenyl)-1,2,3,6-tetrahydro-1,3-dioxo-pyrrolo[3,4-c]carbazole.

5. A pharmaceutical composition for treating heart and blood vessel diseases comprising an effective amount of a compound according to claim 1 in admixture with a pharmaceutically acceptable carrier 6. A method for treating diseases of the heart and blood vessels which comprises treating a mammal suffering therefrom with a pharmaceutical composition according to claim 5 in unit dosage form.

* * * * *

UNITED STATES PATENT AND TRADEMARK OFFICE
CERTIFICATE OF CORRECTION

PATENT NO. : 4,912,107

DATED : March 27, 1990

INVENTOR(S) : Kleinschroth, et al

Page 1 of 2

It is certified that error appears in the above-identified patent and that said Letters Patent is hereby corrected as shown below:

Column 18, line 29, delete "nitro9en" and insert instead -- nitrogen --.

Column 19, line 28, delete "hydroxyl" and insert instead -- hydroxy-1 --.

Column 19, line 42, delete "-3,4-c]" and insert instead -- -[3,4-c] --.

Column 20, line 1, delete "4-(2S".

Column 20, line 3, delete "methyl-" and insert instead -- -6-methyl- --.

Column 20, line 4, delete "3,4-c]" and insert instead -- [3,4-c] --.

Column 20, line 9, delete "1-oxo" and insert instead -- 3-oxo --.

Column 20, line 11, delete "tetrahydro-3" and insert instead -- tetrahydro-1 --.

Column 20, line 20, delete "2 TM aminophenyl" and insert instead -- 2-aminophenyl --.

Col. 20, line 7, delete " 3,4-c]" and insert --[3,4-c]

UNITED STATES PATENT AND TRADEMARK OFFICE
CERTIFICATE OF CORRECTION

PATENT NO. : 4,912,107

DATED : March 27, 1990

INVENTOR(S) : Kleinschroth, et al

It is certified that error appears in the above-identified patent and that said Letters Patent is hereby corrected as shown below:

Column 18, line 67, delete "pyrrolidnylmethoxy" and insert instead -- pyrrolidinylmethoxy --.

Column 19, line 32, delete "ylmethyl" and insert instead -- yl-methyl --.

Column 19, line 32, delete "2-ylmethyl" and insert instead -- 2-yl-methyl --.

Column 19, line 34, delete "2-ylmethyl" and insert instead -- 2-yl-methyl --.

Column 19, line 35, delete "2-ylmethyl" and insert instead -- 2-yl-methyl --.

Signed and Sealed this

Ninth Day of April, 1991

*Attest:*

HARRY F. MANBECK, JR.

*Attesting Officer*  *Commissioner of Patents and Trademarks*